United States Patent [19]

Sprecker et al.

[11] 4,248,787

[45] Feb. 3, 1981

[54] PROCESS FOR PREPARING SUBSTITUTED CYCLIC ACETALS OF OXYACETALDEHYDES AND SAID CYCLIC ACETALS

[75] Inventors: Mark A. Sprecker, Sea Bright; John J. Kryschuk, Howell; John B. Hall, Rumson, all of N.J.

[73] Assignee: International Flavors & Fragrances Inc., New York, N.Y.

[21] Appl. No.: 968,009

[22] Filed: Dec. 8, 1978

Related U.S. Application Data

[60] Division of Ser. No. 902,390, May 3, 1978, which is a continuation-in-part of Ser. No. 811,480, Jun. 30, 1977, abandoned.

[51] Int. Cl.$^2$ ................. C07D 317/10; C07D 319/06; C07D 321/06
[52] U.S. Cl. ................................. 260/338; 260/340.7; 260/340.9 R
[58] Field of Search ..................... 260/340.9 R, 340.7, 260/338

[56] References Cited

U.S. PATENT DOCUMENTS

| | | | |
|---|---|---|---|
| 3,376,315 | 4/1968 | Burger et al. | 260/340.9 R |
| 3,919,252 | 11/1975 | Barker et al. | 260/340.7 X |
| 4,077,982 | 3/1978 | Young et al. | 260/340.7 |
| 4,113,739 | 9/1978 | Truck et al. | 260/340.7 X |

OTHER PUBLICATIONS

Normant, H., Comptes Rendus l'Acad. Sciences 232 (1951), pp. 1942–1945.
Arctander, "Perfume and Flavor Chemicals", vol. 1, 1969, #688.
Arctander, "Perfume and Flavor Chemicals", vol. 1, 1969, #689.
Bedoukian, "Perfumery and Flavoring Synthetics", Elsevir Publishing Co., 2nd Revised Edition, 1967, p. 378.
Eastman Organic Chemicals Bulletin, vol. 48, #1, 1976, p. 2.
Freedman et al., Tetrahedron Letters, No. 38, pp. 3251–3254 (1975).

Primary Examiner—Ethel G. Love
Attorney, Agent, or Firm—Arthur L. Liberman

[57] ABSTRACT

A process is described for the preparation of substituted oxyacetaldehydes and cyclic acetals thereof according to the reaction sequence:

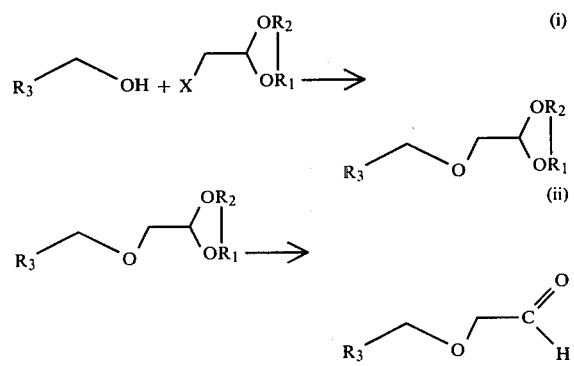

wherein $R_1$ and $R_2$, taken together form a lower alkylene group; wherein $R_3$ is alkyl, alkenyl or alkadienyl and X is halogen selected from the group consisting of chlorine and bromine, the reaction (i) being carried out (1) using a "phase transfer agent" and (2) in a two phase system.

2 Claims, 3 Drawing Figures

IR SPECTRUM FOR EXAMPLE III

IR SPECTRUM FOR EXAMPLE III

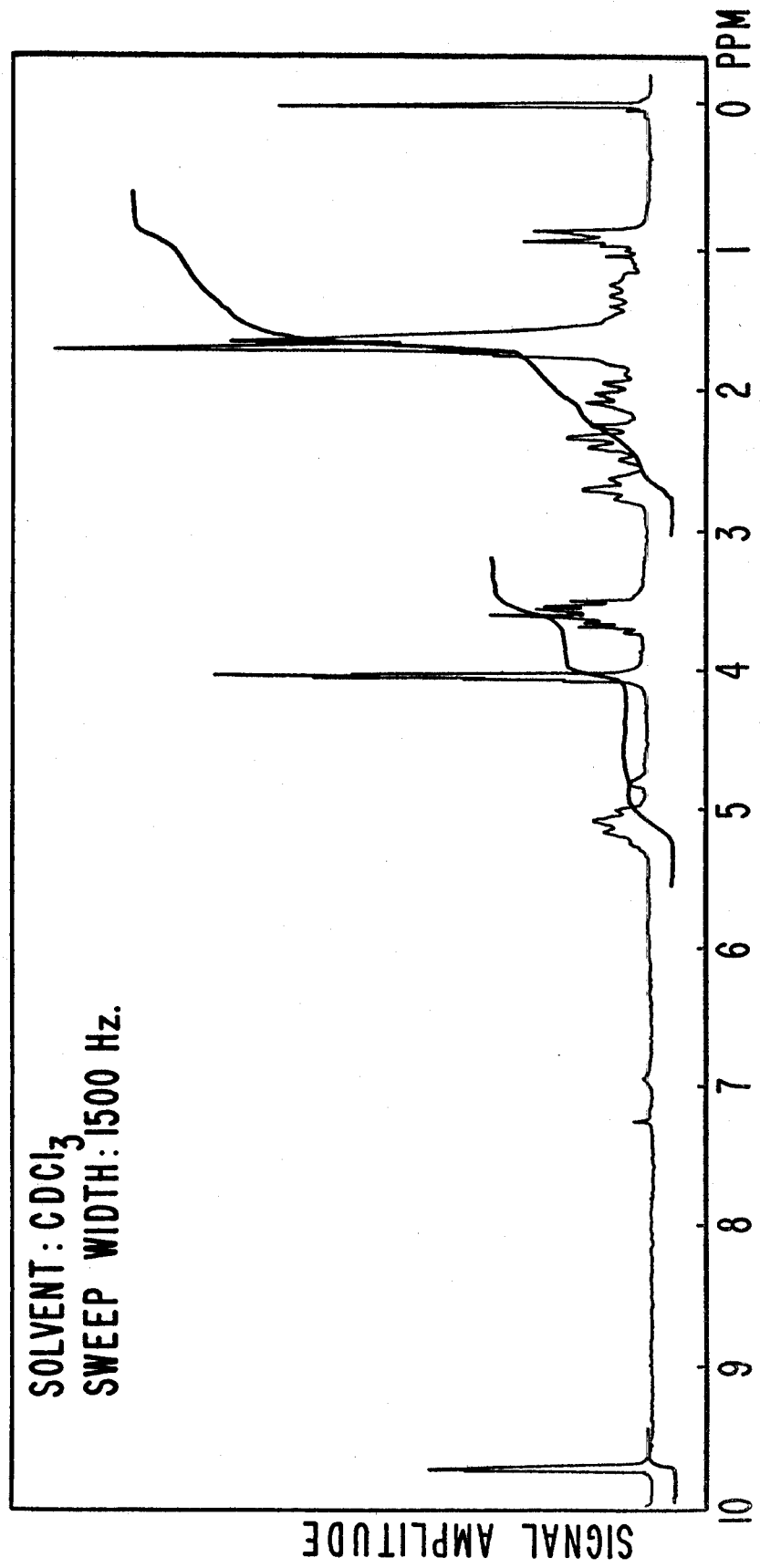

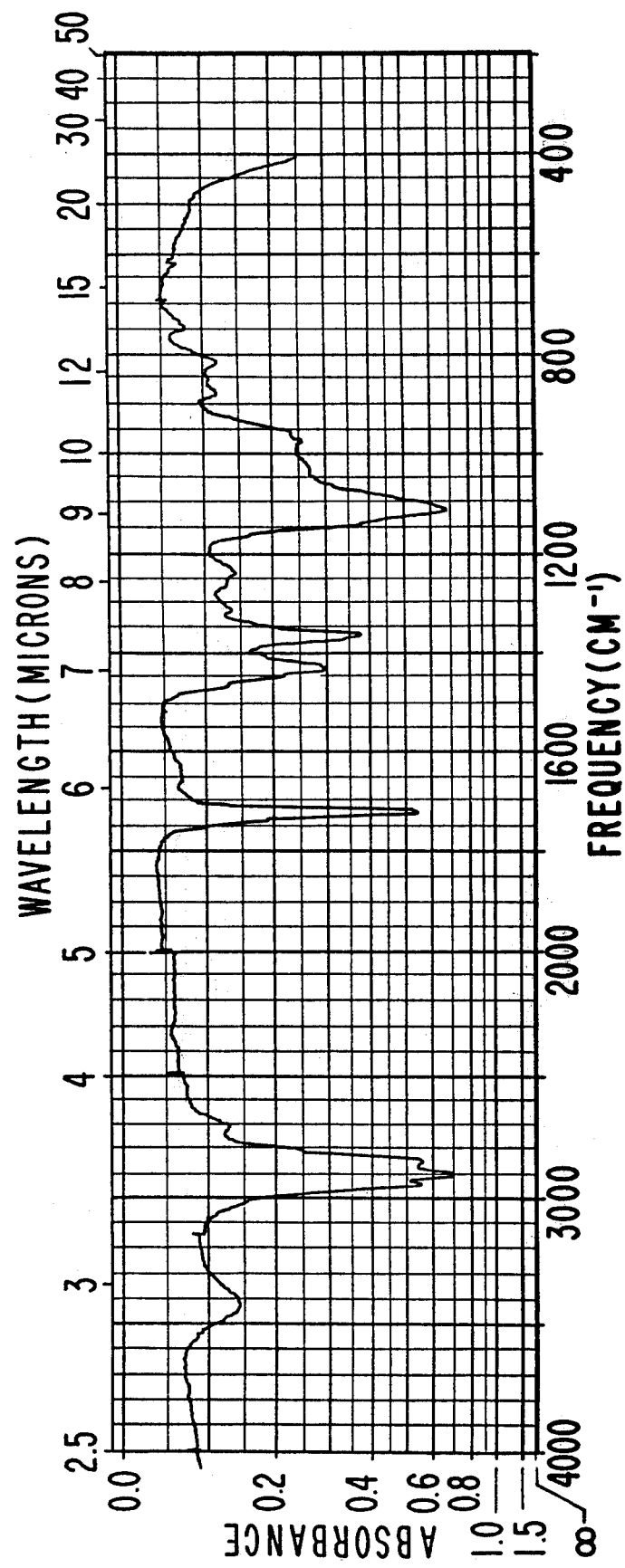

PROCESS FOR PREPARING SUBSTITUTED CYCLIC ACETALS OF OXYACETALDEHYDES AND SAID CYCLIC ACETALS

This is a divisional of application Ser. No. 902,390, filed May 3, 1978, which in turn is a continuation-in-part of application for U.S. Letters Patent Ser. No. 811,480 filed on June 30, 1977, now abandoned.

BACKGROUND OF THE INVENTION

This invention provides processes for preparing certain valuable substances useful in the formation of perfume materials. More specifically, this invention provides a process for preparing substituted oxyacetaldehydes and acetals thereof. The substituted oxyacetaldehydes have the formula:

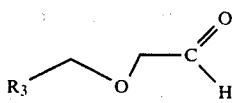

and the substituted oxyacetaldehyde cyclic acetals have the formula:

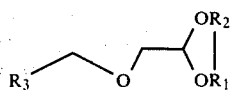

wherein $R_1$ and $R_2$, taken together, represent a lower alkylene moiety; and where $R_3$ is alkyl, alkenyl and alkadienyl.

Examples of the compounds prepared according to the process of this invention are the aldehydes citronellyl oxyacetaldehyde, geranyl oxyacetaldehyde and n-octyl oxyacetaldehyde. Corresponding ethylene; 1,2-propylene; 1,3-propylene; 1,2-butylene; 2,3-butylene; 1,3-butylene and 1,4-butylene acetals are also examples of the compounds prepared according to the process of the instant invention.

Citronellyl oxyacetaldehyde, having the structure:

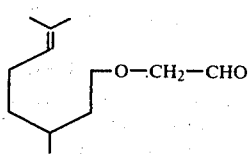

is described by Arctander, "Perfume and Flavor Chemicals" (Aroma Chemicals), Vol. I, 1969, #688. This aldehyde is described as having a "powerful and moderately diffusive green-rosey, sweet Lily-Muguet-like odor". As stated by Arctander, citronellyl oxyacetaldehyde is:

"Used in perfume compositions as a floralizing aldehydic topnote ingredient, primarily in Muguet-Lily fragrances, but also in Rose Peony (where the Geranyl-isomer is claimed to be superior), and various modifications of modern-aldehydic fragrance types.

"Occasionally used in flavor compositions for floral or fruity types, and in Rose type flavors. The concentration is usually mere traces in the finished product."

Arctander states that this material is produced from Citronellol, which is first reacted with Sodium methylate or Sodium iso-propylate. The thus formed Sodium Citronellol organometallic compound is then reacted with Chlorodimethylacetal to produce the citronellyl oxyacetaldehyde dimethylacetal. The thus formed citronellyl oxyacetaldehyde dimethylacetal is finally hydrolyzed with dilute oxalic acid to yield the desired aldehyde, the citronellyl oxyacetaldehyde.

In monograph 689 of Arctander, "Perfume and Flavor Chemicals" (Aroma Chemicals), Vol. I, 1969, Arctander describes citronellyl oxyacetaldehyde diethylacetal having the formula:

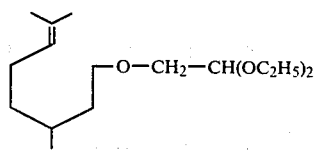

This compound is described as having a "very faint, delicate, Rose-Muguet-type odor". It is also stated to be somewhat more oily and more tenacious than the aldehyde, but much weaker.

Bedoukian, "Perfumery and Flavoring Synthetics", Elsevier Publishing Co., 2nd Revised Edition, 1967, describes at page 378 in the section entitled: "The Oxy-Acetaldehydes" various oxyacetaldehydes for use in perfumery, e.g., citronellyl oxyacetaldehyde, geranyl oxyacetaldehyde, phenylethyl oxyacetaldehyde, benzyl oxyacetaldehyde and decyl oxyacetaldehyde and the corresponding acetals. Bedoukian reports that various references describe the preparation of these oxyacetaldehydes and their acetals by interaction of "bromo acetals with sodium or potassium alcoholates". Thus, Bedoukian states:

"In 1872, Pinner (Ber. 5 (1872) 159) reported the preparation of a number of oxy-acetaldehydes and their acetals by the interaction of bromoacetals with sodium or potassium alcoholates. It was not until 1929, however, that the value of these compounds as perfumery materials was brought to the attention of the industry by Sabetay and co-workers (Bull. Soc. Chim. France, 45 (1929) 1161 and Compt. Rend., 194 (1932) 617 and 196 (1933) 1508). Further work on the preparation of this class of compounds was done by Rothard (Compt. Rend., 196 (1933) 2013; 197 (1933) 1225) and Shoruigin and Korshak (Ber., 68B (1935) 838 and Chem. Abstracts, 29 (1935) 7941), who reported the odor characteristics of many of these compounds."

Neither the references cited by Bedoukian nor the references cited by Arctander disclose the one-step or two-step efficient process of the instant invention (depending on whether acetals or aldehydes are desired to be produced).

In performing the one-step or two-step process of the instant invention, quaternary ammonium salts are used as catalysts or reaction "promoters". Thus, whereas the instant invention discloses and claims the reaction sequence:

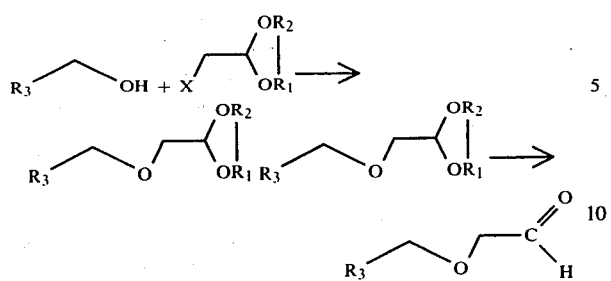

the prior art, as embodied in Bedoukian and Arctander, discloses the three-step reaction sequence, illustrated thusly:

Arctander and Bedoukian Process Disclosed by:

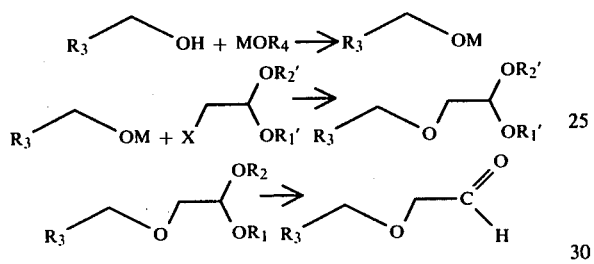

wherein R$_3$ is alkyl, alkenyl or alkadienyl; wherein R$_4$ is lower alkyl; wherein M is potassium or sodium; wherein X is chlorine or bromine and wherein R$_1'$ or R$_2'$ are lower alkyl.

Production of mixed ethers from alkyl halides and alkanols are disclosed using quaternary ammonium salts in the Eastman Organic Chemicals Bulletin, Vol. 48, #1, 1976, page 2, section entitled: "Unsymmetrical Ethers". In addition, the Eastman Organic Chemicals Bulletin discloses the production of aryl alkyl ethers using quaternary ammonium salts. Nevertheless, the production of the alkyl, alkenyl and alkadienyl oxyacetaldehydes and oxyacetaldehyde acetals is not disclosed, either implicitly or explicitly, by either the Eastman Organic Chemicals Bulletin or any of the other prior art where quaternary ammonium salts are used as reaction promoters. Also relevant is the article, Freedman and Dubois, Tetrahedron Letters, No. 38, pages 3251–3254, 1975, "An Improved Williamson Ether Synthesis Using Phase Transfer Catalysis".

THE INVENTION

The invention accordingly comprises the novel process and step or steps, specific embodiments of which are also described hereinafter by use of experiments and in accordance with what is now the preferred practice of the invention.

The process of our invention comprises reacting a primary alcohol having the structure:

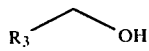

with a halo acetaldehyde acetal having the structure:

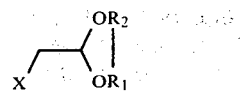

wherein X is chloro or bromo and R$_1$ and R$_2$ taken together, represent lower alkylene, such as ethylene; 1,2-proplyene; 1,3-propylene; 1,2-butylene; 2,3-butylene; 1,3-butylene and 1,4-butylene, to form a substituted oxyacetaldehyde acetal having the structure:

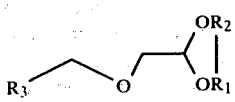

This substituted oxyacetaldehyde cyclic acetal may be used "as is" or if desired, it may then be hydrolyzed to form the substituted oxyacetaldehyde having the structure:

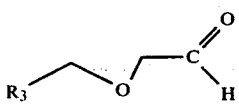

The first reaction to form the ether-acetal takes place in the presence of alkali metal hydroxides and one or more "phase transfer agents". The reaction is carried out in a two-phase system in the absence of a solvent or the presence of an inert solvent.

More specifically, the first step of our invention provides a process for the etherification of alkanols, alkenols and alkadienols with halogenated acetaldehyde cyclic C$_2$–C$_4$ acetals under the influence of a base comprising the step of placing the reactants for the process and the base respectively in two immiscible phases; an organic phase and a solid base phase with the reactants being located substantially entirely in the first mentioned organic phase and the base being located substantially entirely in the second mentioned phase; and adding to the two phase system a "phase transfer agent" which may be one or more of several organic quaternary ammonium salts.

Specific examples of "phase transfer agents" useful in our invention are as follows:
Tricapryl methyl ammonium chloride;
Cetyl trimethyl ammonium bromide; and
Benzyl trimethyl ammonium hydroxide.

In general, the "phase transfer agents" most preferred have the generic formula:

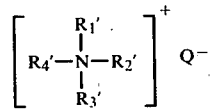

wherein at least one of R$_1'$, R$_2'$, R$_3'$ and R$_4'$ is C$_6$–C$_{14}$ aryl, C$_6$–C$_{10}$ alkaryl, C$_6$–C$_{20}$ alkyl, C$_6$–C$_{14}$ aralkyl and C$_6$–C$_{20}$ alkenyl and the other of R$_2'$, R$_3'$ and R$_4'$ is alkyl such as methyl, ethyl, n-propyl, i-propyl, 1-butyl, 2-butyl, 1-methyl-2-propyl, 1-pentyl and 1-octyl and Q$^-$ is an anion such as chloride, bromide and hydroxide.

The process of our invention is carried out at a temperature in the range of from about 120° C. up to about 200° C. with a temperature range of about 135°–145° C.

being preferred. The reaction time is inversely proportional to the reaction temperature, with lower reaction temperatures giving rise to greater reaction times; and, accordingly, the reaction time ranges from about 5 hours up to 14 hours. It is noteworthy that excessive reaction times are not preferred due to the formation of a side product which is a trialkoxy ethane having the generic structure:

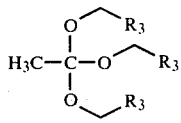

In the reaction of our invention the mole ratio of hydroxy compound (having the formula:

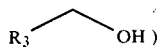

to halo acetaldehyde cyclic acetal (having the structure:

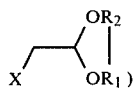

is preferably about 1:1, but may vary between 0.5:1 to 2:1. In the reaction of our invention the mole ratio of said hydroxy compound to base is preferably about 1:1.5, but may vary between 1:1 and 1:2. In any event, it is preferable to use an excess of base with respect to hydroxyl compound having the structure:

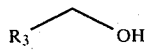

The quantity of "phase transfer agent" in the reaction mass based on amount of halogenated acetaldehyde cyclic acetal in the reaction mass may vary from 0.5 grams per mole of halogenated acetaldehyde cyclic acetal up to 25 grams of "phase transfer agent" per mole of halogenated acetaldehyde cyclic acetal, with a preferred concentration of "phase transfer agent" being in the range of from about 2.5 up to about 7.5 grams of "phase transfer agent" per mole of halogenated acetaldehyde cyclic acetal.

The reaction of our invention is preferably carried out at atmospheric pressure since that is the most convenient condition. However, lower or higher pressures can be used without detrimentally affecting the ultimate yield of desired product.

In the single step etherification reaction, bases used in said reaction are sodium hydroxide and potassium hydroxide.

Certain bases will not give rise to any reaction, e.g., lithium hydroxide, calcium hydroxide or barium hydroxide.

The etherification reaction of the process of our invention is preferably best carried out in the absence of solvent; however, solvents such as xylene or higher boiling hydrocarbons, e.g. decalin can be used, but use of such solvents slows down the rate of reaction. In any event, alcohols and halogenated chlorocarbon solvents such as dichlorobenzene should not be used as a reaction solvent. Furthermore, toluene and benzene should not be used as the etherification reaction solvent, since the temperature of reaction must be above 120° C. and the use of such solvents at atmospheric pressure, in particular, will cause the reaction not to take place.

Examples of cyclic acetals produced using the process of our invention are as follows:
Citronellyl oxyacetaldehyde ethylene glycol acetal;
Citronellyl oxyacetaldehyde-1,2-propylene glycol acetal;
Citronellyl oxyacetaldehyde-1,3-propylene glycol acetal;
Citronellyl oxyacetaldehyde-1,2-butylene diol acetal;
Citronellyl oxyacetaldehyde-1,3-butylene diol acetal;
Citronellyl oxyacetaldehyde-1,4-butylene diol acetal;
Citronellyl oxyacetaldehyde-2,3-butylene diol acetal;
Geranyl oxyacetaldehyde ethylene glycol cyclic acetal;
Geranyl oxyacetaldehyde-1,2-propylene glycol cyclic acetal;
Geranyl oxyacetaldehyde-1,3-propylene glycol cyclic acetal;
Geranyl oxyacetaldehyde-1,2-butylene diol cyclic acetal;
Geranyl oxyacetaldehyde-1,3-butylene diol cyclic acetal;
Geranyl oxyacetaldehyde-1,4-butylene diol cyclic acetal;
Geranyl oxyacetaldehyde-2,3-butylene diol cyclic acetal;
Octyloxyacetaldehyde ethylene glycol cyclic acetal;
Octyloxyacetaldehyde-1,2-propylene glycol cyclic acetal;
Octyloxyacetaldehyde-1,3-propylene glycol cyclic acetal;
Octyloxyacetaldehyde-1,2-butylene diol cyclic acetal;
Octyloxyacetaldehyde-1,3-butylene diol cyclic acetal;
Octyloxyacetaldehyde-1,4-butylene diol cyclic acetal;
Octyloxyacetaldehyde-2,3-butylene diol cyclic acetal;

The resulting substituted oxyacetaldehyde cyclic acetals may be used in perfumery or in perfumed articles as such or they may be, if desired, hydrolyzed to their corresponding aldehydes. The hydrolysis step of the reaction sequence of our invention may be carried out under standard conditions with the exception that care must be taken that when the acetal moiety is hydrolyzed, the ether linkage is not cleared. Accordingly, the particular hydrolysis reagents used for hydrolyzing the acetal are critical. Thus, for example, oxalic acid, dilute aqueous hydrochloric acid, dilute aqueous sulfuric acid or aqueous formic acid, may be used to hydrolyze the acetal to the corresponding aldehydes.

As a general rule, the preferable reactions of our invention are illustrated by the following reaction sequence:

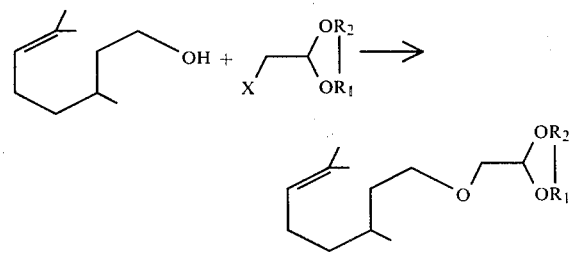

-continued

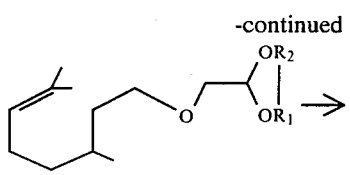

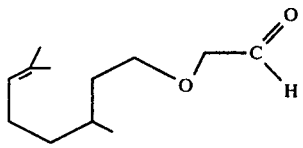

wherein X is chloro or bromo, and R₁ and R₂, taken together, form a lower alkylene moiety such as 1,2-ethylene; 1,2-propylene; 1,3-propylene; 1,2-butylene; 2,3-butylene; 1,3-butylene and 1,4-butylene. More specifically, the reactions of our invention are illustrated most preferably by the following reaction sequences:

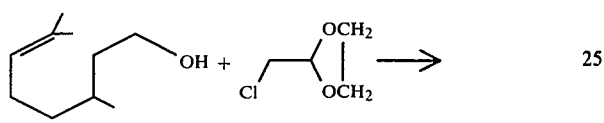

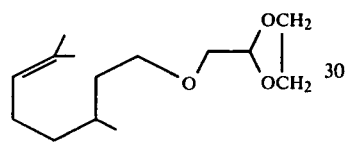

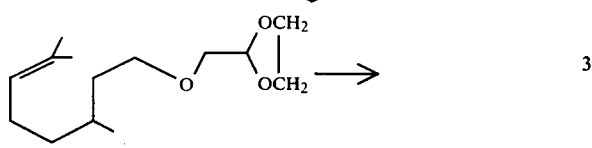

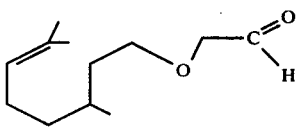

(production of citronellyl oxyacetaldehyde ethylene glycol acetal followed by production of citronellyl oxyacetaldehyde);

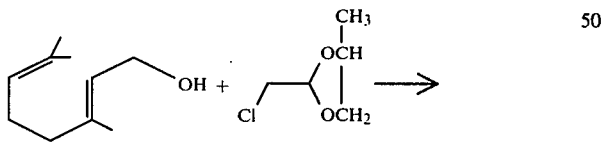

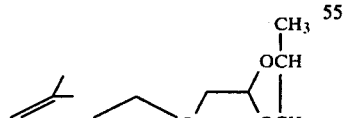

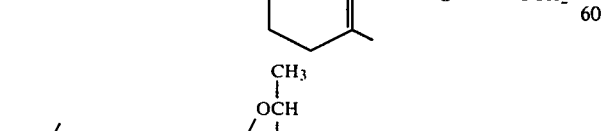

-continued

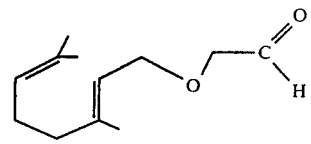

(production of geranyl oxyacetaldehyde 1,2-propylene glycol cyclic acetal followed by production of geranyl oxyacetaldehyde); and

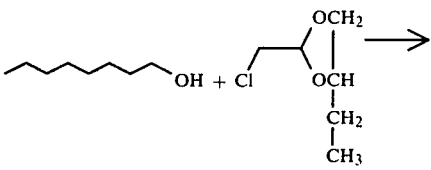

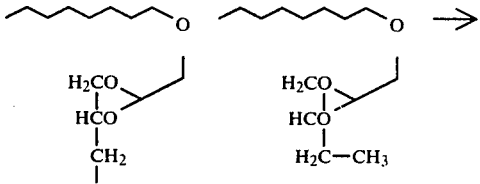

(production of octyl oxyacetaldehyde dimethylacetal followed by production of octyl oxyacetaldehyde).

The following Examples I, II and III serve to illustrate embodiments of our invention as it is now preferred to practice it. Example IV illustrates the utility of one of the compounds produced according to the process of our invention. It will be understood that these Examples are illustrative and restricted thereto only as defined in the appended claims.

EXAMPLE I

Preparation of Citronellyl Oxyacetaldehyde Ethylene Glycol Cyclic Acetal

Reaction:

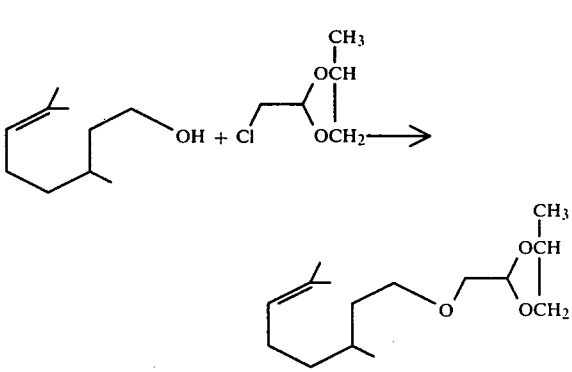

A mixture of 3050 grams of citronellol (containing approximately 10% of 3,7-dimethyl octanol), 1200 grams of granular sodium hydroxide and 95 grams of Aliquat 336 ® (registered trademark of General Mills Chemicals, Inc., identifying tricapryl methyl ammonium chloride) is heated to 140° C. with vigorous stirring. 2732 Grams of chloroacetaldehyde 1,2-propylene glycol cyclic acetal are then added over a 30 minute period and the mixture is heated at reflux for a period of 7 hours. 5 Liters of water is added to the cooled reaction mass and stirring is continued until all solids are dissolved. The aqueous phase is discarded and 300 ml of toluene, 75 grams of Primol ® and 0.2 grams of Ionox ® are added to the organic phase. Distillation affords 2142 grams of recovered citronellol (boiling point 88° C. at 5 mm Hg pressure) and 2150 grams of citronellyl oxyacetaldehyde 1,2-propylene glycol cyclic acetal.

EXAMPLE II

Preparation of n-Octyl Oxyacetaldehyde Dimethyl Acetal

Reaction:

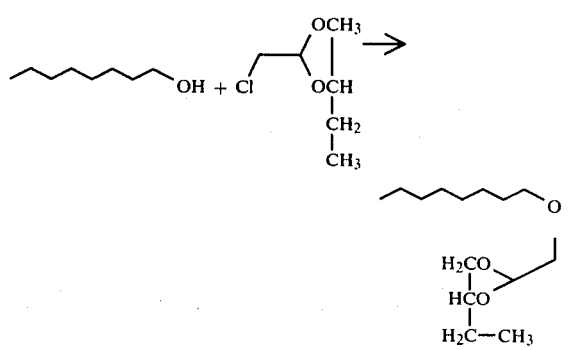

A mixture of 130 grams of n-octanol, 60 grams of granular sodium hydroxide, 4 grams of Aliquat 336 ® (registered trademark of General Mills Chemicals, Inc.) and 140 grams of chloro acetaldehyde 1,2-butylene glycol cyclic acetal are heated to reflux for 4 hours. The reaction mass is cooled and 200 ml of water are added thereto with vigorous stirring. After all solids are dissolved, the aqueous phase is distilled to yield 87 grams of n-octanol (boiling point 60° C. at 1.4 mm Hg pressure) and 85 grams of n-octyl oxyacetaldehyde 1,2-butylene glycol cyclic acetal.

EXAMPLE III

Preparation of Geranyl/Neryl Oxyacetaldehyde Dimethyl Acetal

Reaction:

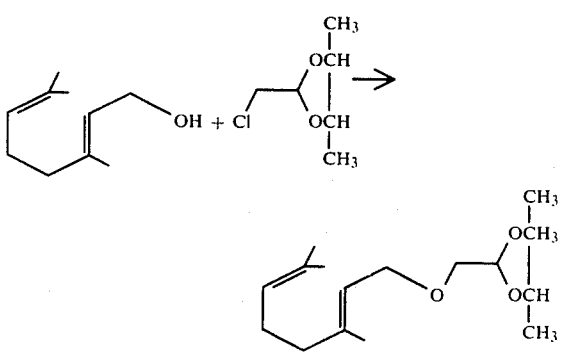

A mixture of 770 grams of geraniol (containing nerol), 360 grams of chloroacetaldehyde 2,3-butylene glycol cyclic acetal, 150 grams of granular sodium hydroxide and 25 grams of Aliquat 336 ® (registered trademark of General Mills Chemicals, Inc.) is heated at reflux for 13 hours. The reaction mass is cooled to room temperature and 500 ml of water are added with vigorous stirring. The organic phase is distilled through a 1"×12" Goodloe packed column using a reflux ratio of 4:1 after adding to the reaction mass 50 grams of toluene, 10 grams of Primol ® and 0.1 grams of Ionox ®, affording 460 grams of geranyl/neryl oxyacetaldehyde 2,3-butylene glycol cyclic acetal.

The mixture of geranyl oxyacetaldehyde 2,3-butylene glycol cyclic acetal and neryl oxyacetaldehyde 2,3-butylene glycol cyclic acetal is separated using preparative GLC (conditions: 10% SE-30 column, 10'×¼", isothermal operated at 220° C.). The geranyl oxyacetaldehyde 2,3-butylene glycol cyclic acetal is thus separated from the neryl oxyacetaldehyde 2,3-butylene glycol cyclic acetal.

EXAMPLE IV

Preparation of Geranyl Oxyacetaldehyde

Reaction:

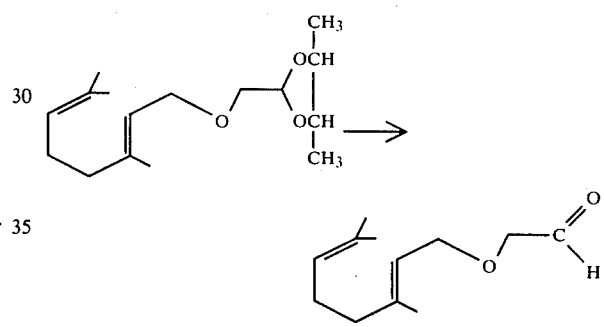

Into a 1 liter reaction flask equipped with thermometer, stirrer, heating mantle and reflux condenser is placed the following materials:

| | |
|---|---|
| Geranyl oxyacetaldehyde 2,3-butylene glycol cyclic acetal | 390 grams |
| Formic acid | 300 grams |
| Water | 900 grams |

The reaction mass is heated to 80° C. for a period of 6 hours with GLC samples (200° C. isothermal SE-30 column) taken every 90 minutes. At the end of the 6 hour period, 1.33 liters of water is added to the reaction mass. Sodium bicarbonate is added to the organic phase to a pH of 7. 200 ml benzene is then added to the organic phase. 10 Grams of Primol ® is also added and the resulting material is distilled yielding 120 grams of geranyl oxyacetaldehyde (boiling point 115°-112° C. at 3 mm Hg). The reaction product, at the end of the rushover, is analyzed by means of GLC analysis. The GLC profile is set forth in FIG. 1.

The NMR spectrum for the mixture of geranyl oxyacetaldehyde and neryl oxyacetaldehyde is set forth in FIG. 2.

The Infrared spectrum for the mixture of geranyl oxyacetaldehyde and neryl oxyacetaldehyde is set forth in FIG. 3.

EXAMPLE V

Muguet Formulation

The following perfume formulation is prepared:

| Ingredients | Parts by Weight |
| --- | --- |
| Benzyl Acetate | 25 |
| Linalol | 30 |
| Dimethyl benzyl carbinol | 50 |
| Oil of Bergamot | 20 |
| Citronellyl Formate | 20 |
| Rhodinol | 150 |
| Heliotropin | 40 |
| Ylang | 10 |
| Cinnamic Alcohol | 150 |
| Hydroxy Citronellyl | 250 |
| Mixture of geranyl oxyacetaldehyde and neryl oxyacetaldehyde prepared according to Example IV | 12 |
| Citronellyl oxyacetaldehyde ethylene glycol cyclic acetal prepared according to Example I | 8 |

The addition to the above formulation of the citronellyl oxyacetaldehyde ethylene glycol cyclic acetal prepared according to Example I, and the mixture of geranyl oxyacetaldehyde and neryl oxyacetaldehyde prepared according to Example IV, enhances the muguet note of this muguet formulation.

FIG. 2 is the NMR spectrum for the mixture of geranyl oxyacetaldehyde and neryl oxyacetaldehyde produced according to Example IV.

FIG. 3 is the Infrared spectrum for the mixture of geranyl oxyacetaldehyde and neryl oxyacetaldehyde produced according to Example IV.

Figure 1:
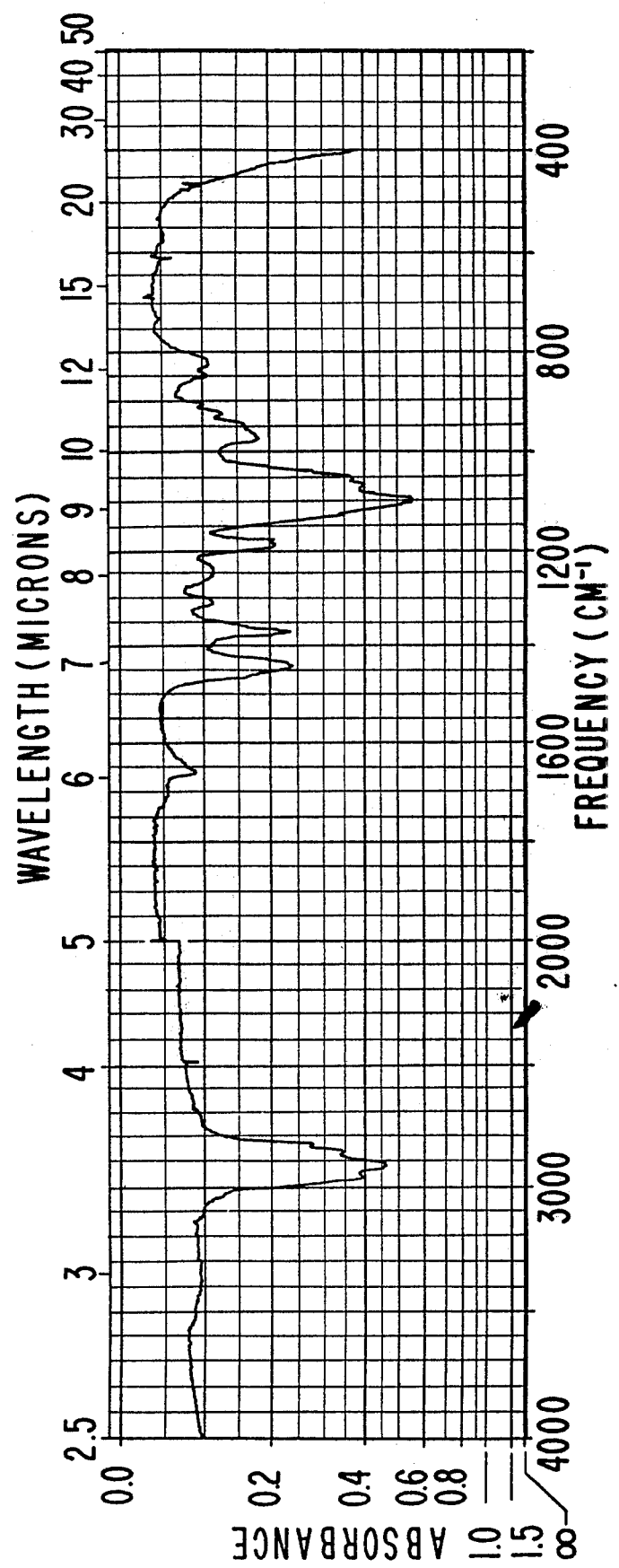
FIG. 1 is the GLC profile for the reaction product of Example IV containing a mixture of geranyl oxyacetaldehyde and neryl oxyacetaldehyde.

What is claimed is:

1. A process for preparing citronellyl oxyacetaldehyde alkylene acetal according to the reaction:

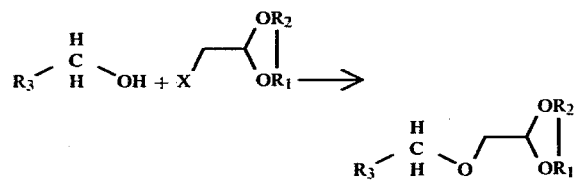

comprising the steps of (a) intimately admixing citronellol with chloroacetaldehyde alkylene acetal in the presence of a base which is sodium hydroxide and a phase transfer agent which is tricapryl methyl ammonium chloride; the reaction temperature being in the range of from 120° C. up to about 200° C.; the mole ratio of citronellol to chloroacetaldehyde alkylene acetal being from 0.5:1 up to 2:1, the mole ratio of citronellol to base being between 1:1 and 1:2; the concentration of tricapryl methyl ammonium chloride phase transfer agent in the reaction mass based on amount of chloroacetaldehyde alkylene acetal being in the range of from 0.5 grams of tricapryl methyl ammonium chloride per mole of chloroacetaldehyde alkylene acetal up to 25 grams of tricapryl methyl ammonium chloride per mole of chloroacetaldehyde alkylene acetal; the reaction being carried out in the absence of solvent or in the presence of a solvent selected from the group consisting of xylene and decalin; and (b) fractionally distilling the resulting product hereby citronellyl oxyacetaldehyde alkylene acetal is recovered from the distillate; wherein

is the citronellyl moiety; wherein $R_1$ and $R_2$ taken together form an alkylene moiety having from 2 up to 4 carbon atoms and wherein X is chloro.

2. A process for preparing a mixture of geranyl oxyacetaldehyde and neryl oxyacetaldehyde according to the reaction sequence:

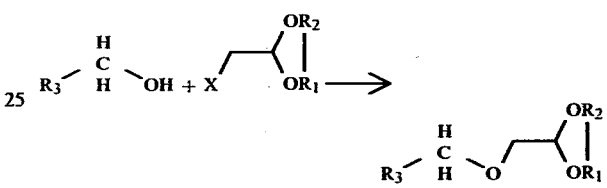

comprising the steps of (a) intimately admixing a mixture of geraniol and nerol with chloroacetaldehyde alkylene acetal in the presence of a base which is sodium hydroxide and a phase transfer agent which is tricapryl methyl ammonium chloride; the reaction temperature being in the range of from 120° C. up to about 200° C.; the mole ratio of mixture of geraniol and nerol to chloroacetaldehyde alkylene acetal being from 0.5:1 up to 2:1; the mole ratio of mixture of nerol and geraniol:base being from 1:1 up to 1:2; the concentration of tricapryl methyl ammonium chloride in the reaction mass based on amount of chloroacetaldehyde alkylene acetal being in the range of from 0.5 grams of tricapryl methyl ammonium chloride per mole of chloroacetaldehyde alkylene acetal up to 25 grams of tricapryl methyl ammonium chloride per mole of chloroacetaldehyde alkylene acetal; the reaction being carried out in the absence of solvent or in the presence of a solvent selected from the group consisting of xylene and decalin; (b) then fractionally distilling the resulting product whereby the mixture of geraniol oxyacetaldehyde alkylene acetal and nerol oxyacetaldehyde alkylene acetal is recovered from the distillate; wherein

represents the geranyl or neryl moiety; wherein $R_1$ and $R_2$ taken together represent alkylene of from 2 up to 4 carbon atoms; and wherein X is chloro.

* * * * *